(12) United States Patent
Peng (10) Patent No.: US 11,491,285 B2
(45) Date of Patent: Nov. 8, 2022

(54) ULTRASONIC MEDICINE APPLICATION DEVICE THAT STRONGLY PROMOTES MEDICINE ABSORPTION

(71) Applicant: Zhijun Peng, Guangdong (CN)

(72) Inventor: Zhijun Peng, Guangdong (CN)

( * ) Notice: Subject to any disclaimer, the term of this patent is extended or adjusted under 35 U.S.C. 154(b) by 257 days.

(21) Appl. No.: 16/824,653

(22) Filed: Mar. 19, 2020

(65) Prior Publication Data

US 2020/0353182 A1 Nov. 12, 2020

(30) Foreign Application Priority Data

May 6, 2019 (CN) .......................... 201910370047.X (51) Int. Cl.
*A61M 11/00* (2006.01)
*A61M 11/04* (2006.01)

(52) U.S. Cl.
CPC .......... *A61M 11/005* (2013.01); *A61M 11/007* (2014.02); *A61M 11/042* (2014.02); *A61M 2205/33* (2013.01); *A61M 2205/36* (2013.01)

(58) Field of Classification Search
CPC .............. A61M 11/005; A61M 11/007; A61M 11/042; A61M 2205/33; A61M 2205/36; A61M 35/003; A61M 2037/0007; A61M 11/02; A61M 2205/106; A61M 2205/3569; A61M 2210/04; A61M 11/006; A61M 2202/0468; A61M 37/0092; A61M 2202/06; A61M 2205/07; A61M 2205/3368; A61M 2205/3592; A61M 2205/505; A61M 2209/088; A61H 2201/105; A61H 2201/1207; A61H 2201/165; A61H 2201/1695; A61H 23/0254; A61H 2201/5007; A61H 2201/5046; A61H 2201/5097; A61H 1/00; A61H 23/0245

See application file for complete search history.

(56) References Cited

U.S. PATENT DOCUMENTS

| | | | | |
|---|---|---|---|---|
| 5,972,290 | A * | 10/1999 | De Sousa | A61L 9/125 422/123 |
| 8,932,198 | B1 * | 1/2015 | You | A61B 50/13 600/27 |
| 11,123,577 | B2 * | 9/2021 | Blanche | A61H 23/0245 |
| 2006/0260609 | A1 * | 11/2006 | Bruening | A61M 11/041 128/200.24 |
| 2010/0319687 | A1 * | 12/2010 | Esaki | A61M 15/0018 128/200.23 |

FOREIGN PATENT DOCUMENTS

CN 109330867 A * 2/2019 ............. A61H 33/06

* cited by examiner

*Primary Examiner* — Justine R Yu
*Assistant Examiner* — Matthew R Moon (57) ABSTRACT

An ultrasonic medicine application device that strongly promotes medicine absorption, having a housing, a control panel and a circuit board inside the housing, a medicine supply mechanism and an ultrasonic massage mechanism on a bottom surface of the housing. The ultrasonic massage mechanism has a base panel having massage projections, and also an electrical ultrasonic vibration element, which drives the projections make high frequency ultrasonic vibration. The medicine supply mechanism is positioned between the ultrasonic massage mechanism and the circuit board, and is configured to supply medicine towards the ultrasonic massage mechanism.

4 Claims, 11 Drawing Sheets

ULTRASONIC MEDICINE APPLICATION DEVICE THAT STRONGLY PROMOTES MEDICINE ABSORPTION

BACKGROUND OF THE INVENTION

The present invention relates to the field of electrical products used as medicinal therapy aid, and more specifically relates to an electrical medicine application device.

In the field of traditional Chinese medicinal therapy, moxibustion is the most traditional means and a commonly used method in Chinese medicinal therapy and general health maintenance. Moxibustion makes use of the heat of burning *Artemisia argyi* (Mugwort) felt through a patient's skin to achieve various health benefits such as warming and clearing of the patient's meridian system, activating qi (vital energy) and stimulating blood flow of the body, mitigating dampness and coldness, soothing menstrual pain, balancing yin and yang, promoting blood circulation, and regulating internal organs. In general, moxibustion can effectively facilitate human body metabolism and strengthen our immune system. Nowadays, an electrical therapeutic product that adopts electrical heating for the purpose of moxibustion can be occasionally found in the market, and such product is operated by means of PTC heating, wherein mugwort is first processed into a solid mugwort cake, during use, the mugwort cake is placed on the PTC heater trough of the product to heat up the mugwort cake such that molecules of the mugwort can be volatilized and released to warm the patient's skin. The electrical principle of this kind of prior art product has substantially no difference from that of electrical mosquito repellent and repellent plate. Compared with even more traditional means of carrying out moxibustion, this kind of prior art product can effectively prevent harmful effect to the lung and to the indoor environment due to the smoke produced by burning mugwort, thereby simplifying the procedure of moxibustion and reducing injuries caused by the burning mugwort, however, the therapeutic effects achieved by this kind of prior art product are not greatly enhanced compared to traditional moxibustion. After all, this kind of prior art product is still making use of rising temperature which allows expansion of skin pores following the gradual increase of warming temperature, so that the skin is passively warmed by the heat of mugwort to achieve the therapeutic effects of moxibustion. This kind of passive warming of the skin by the heat of mugwort is deficient largely because of its low effectiveness and poor results. Hence, patients are required to passively receive a longer period of moxibustion treatment before getting some results. Therefore, patients are required to spend more time and money before they can experience some therapeutic effects.

BRIEF SUMMARY OF THE INVENTION

In view of the aforesaid disadvantages now present in the prior art, the present invention provides an ultrasonic medicine application device that strongly promotes medicine absorption. The device can on one hand apply high frequency ultrasonic massage to the patient's body, and on the other hand apply medicinal therapy. Due to high frequency ultrasonic massage, blood flow of the body can be speeded up, causing quick increase in temperature of the body part being massaged, thus the skin pores thereon will be quickly expanded to actively receive warming from the medicinal molecules. Therefore, therapeutic components of the medicine can quickly and effectively get into the patient's skin to demonstrate the therapeutic effects of the medicine. Thus, the therapeutic results of the medicine can be significantly improved, and the time period for treatment can be significantly shortened, thereby saving time and money for the patients.

The present invention is achieved as follows: An ultrasonic medicine application device that strongly promotes medicine absorption, comprising a housing, a control panel, a circuit board, a medicine supply mechanism, and an ultrasonic massage mechanism; wherein the control panel is provided on a surface of the housing; the circuit board is mounted inside the housing; the control panel and the circuit board are electrically connected; the ultrasonic massage mechanism is provided at a bottom surface of the housing; the ultrasonic massage mechanism comprises a base panel having massage projections, and an electrical ultrasonic vibration element provided on the base panel; the electrical ultrasonic vibration element is electrically connected with the circuit board; the massage projections make high frequency ultrasonic vibration when being driven by the electrical ultrasonic vibration element; the electrical ultrasonic vibration element is a high frequency vibrating motor or an ultrasonic transducer; the medicine supply mechanism is mounted inside the housing between the circuit board and the ultrasonic massage mechanism, and is electrically connected with the circuit board; the medicine supply mechanism is configured to supply medicine towards the ultrasonic massage mechanism; a plurality of through holes are provided on the base panel so that the medicine can pass through the through holes; the medicine supply mechanism is implemented as an electrically heating and volatilizing device for solid form medicine, comprising a medicine chamber, an electrical heating plate, and a supporting shell; or the medicine supply mechanism is implemented as a liquid form medicine spraying device, comprising a liquid storage box, a liquid suction pump and a plurality of mist spray nozzles 46; or the medicine supply mechanism is implemented as an ultrasonically atomized liquid form medicine spraying device, comprising a supporting shell, a liquid storage box, and an ultrasonic atomizing module; or the medicine supply mechanism is implemented as an electrical heating and volatilizing device for liquid form medicine, comprising a supporting shell, a liquid storage container, an electrical heating ring, and a liquid suction body, wherein one end of the liquid suction body is configured to be inserted into the liquid storage container, and another end of the liquid suction body is configured to be sleeved within the electrical heating ring.

The present invention has the following beneficial effects: The present invention provides specific structural implementations of the medicine supply mechanism to operate cooperatively with the ultrasonic massage mechanism, such that during use of the device of the present invention, the device can on one hand apply high frequency ultrasonic massage to the patient's body, and on the other hand apply medicinal therapy. Due to high frequency ultrasonic massage, blood flow of the body can be speeded up, causing quick increase in temperature of the body part being massaged, thus the skin pores thereon will be quickly expanded to actively receive warming from the medicinal molecules. Therefore, therapeutic components of the medicine can quickly and effectively get into the patient's skin to demonstrate the therapeutic effects of the medicine. Thus, the therapeutic effects of the medicine can be significantly enhanced, and the time period for treatment can be significantly shortened, thereby saving time and money for the patients.

DETAILED DESCRIPTION OF THE INVENTION

As shown in FIGS. 1 to 15, the present invention is an ultrasonic medicine application device that strongly promotes medicine absorption, mainly comprising several functional components including a housing 1, a control panel 2, a circuit board 3, a medicine supply mechanism 4, and an ultrasonic massage mechanism 5.

As shown in FIGS. 1, 4, 7, 10 and 13, the control panel 2 is provided on a surface of the housing 1. This surface of the housing 1 can be a top surface of the housing 1 or a side surface of the housing 1. The control panel 2 may comprise mechanical press switches or may be a touch screen panel. In order to show functional messages to users clearly and unambiguously during operation, the control panel 2 may also comprise an LCD display 21.

As shown in FIGS. 2, 5, 8, 11 and 14, the circuit board is mounted inside the housing 1. Specifically, the circuit board 3 is placed in a circuit board chamber 15 provided inside the housing 1. The control panel 2 and the circuit board 3 are electrically connected.

As also shown in FIGS. 2, 5, 8, 11 and 14, the ultrasonic massage mechanism 5 is provided at a bottom surface of the housing 1; the ultrasonic massage mechanism 5 comprises a base panel 51 having massage projections 511, and an electrical ultrasonic vibration element 52 provided on the base panel 51; the electrical ultrasonic vibration element 52 is electrically connected with the circuit board 3, and is operated according to the concentrated controlling from the circuit board 3. The massage projections 511 make high frequency ultrasonic vibration when being driven by the electrical ultrasonic vibration element 52. The electrical ultrasonic vibration element 52 is a high frequency vibrating motor or an ultrasonic transducer. In case of high frequency vibrating motor, the motor has a rotating speed of 10,000 rpm. In case of ultrasonic transducer, the vibration frequency is above 1 MHz. Quantity of the high frequency vibrating motor or the ultrasonic transducer provided will increase or decrease depending on the size and specification of the ultrasonic medicine application device, on condition that the vibration frequency of the massage projections 511 is always above 1 Mhz. The vibration frequency of the massage projections 511 can be measured by a vibration measuring instrument. If the ultrasonic transducer is used, the circuit board 3 is also provided with an ultrasonic generator or an ultrasonic generator circuit.

As also shown in FIGS. 2, 5, 8, 11 and 14, the medicine supply mechanism 4 is mounted inside the housing 1 between the circuit board 3 and the ultrasonic massage mechanism 5, and is electrically connected with the circuit board 3. Under concentrated control by the circuit board 3, the medicine supply mechanism 4 operates cooperatively with the ultrasonic massage mechanism 5. The medicine supply mechanism 4 is configured to supply medicine towards the ultrasonic massage mechanism 5. A plurality of through holes 53 are provided on the base panel 51 so that the medicine can pass through the through holes 53. In other words, the through holes 53 are provided such that molecules of the medicine can be in contact with the patient's skin.

Besides, two ears 16 each having an opening for a string to pass through are provided respectively at two sides of the housing 1. As a result, the two ears 16 are each provided to be tied with a string so that during therapy, the present invention is tied via the string at the body part targeted for therapy. During use, the ultrasonic massage mechanism 5 is disposed towards and attached firmly to the targeted body part to perform ultrasonic vibration massage. Besides, the present invention can be implemented in combination with wearable items of various forms or structures, so that the present invention is embodied as a wearable ultrasonic medicine application device that can be worn on the patient's body. Said wearable items can be any common items including various clothes, trousers, head wearing items, neck wearing items, socks and gloves etc.

Figure 1:
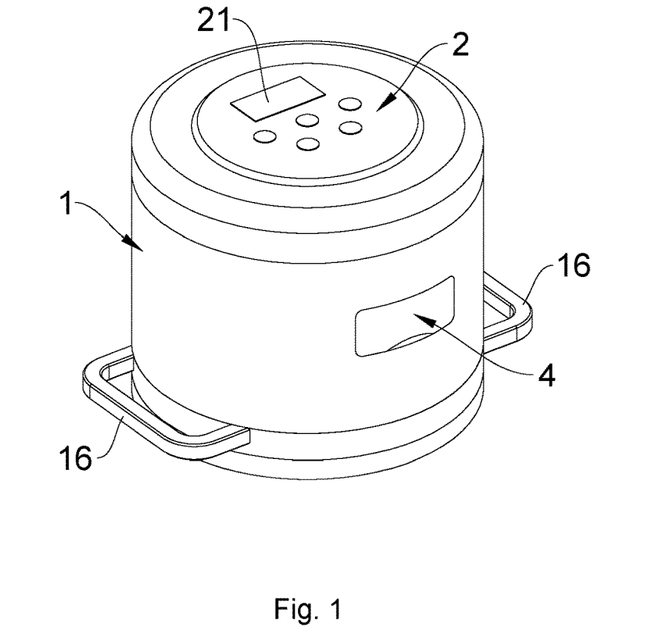
FIG. 1 is a perspective structural view according to embodiment 1 of the present invention.
Figure 2:
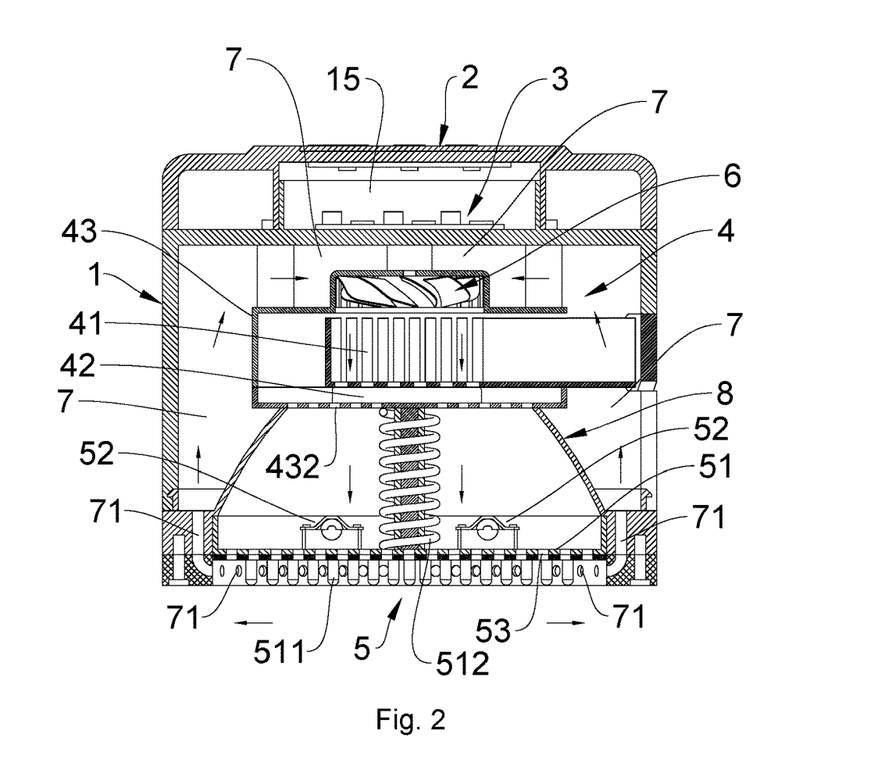
FIG. 2 is a sectional structural view according to embodiment 1 of the present invention.
Figure 3:
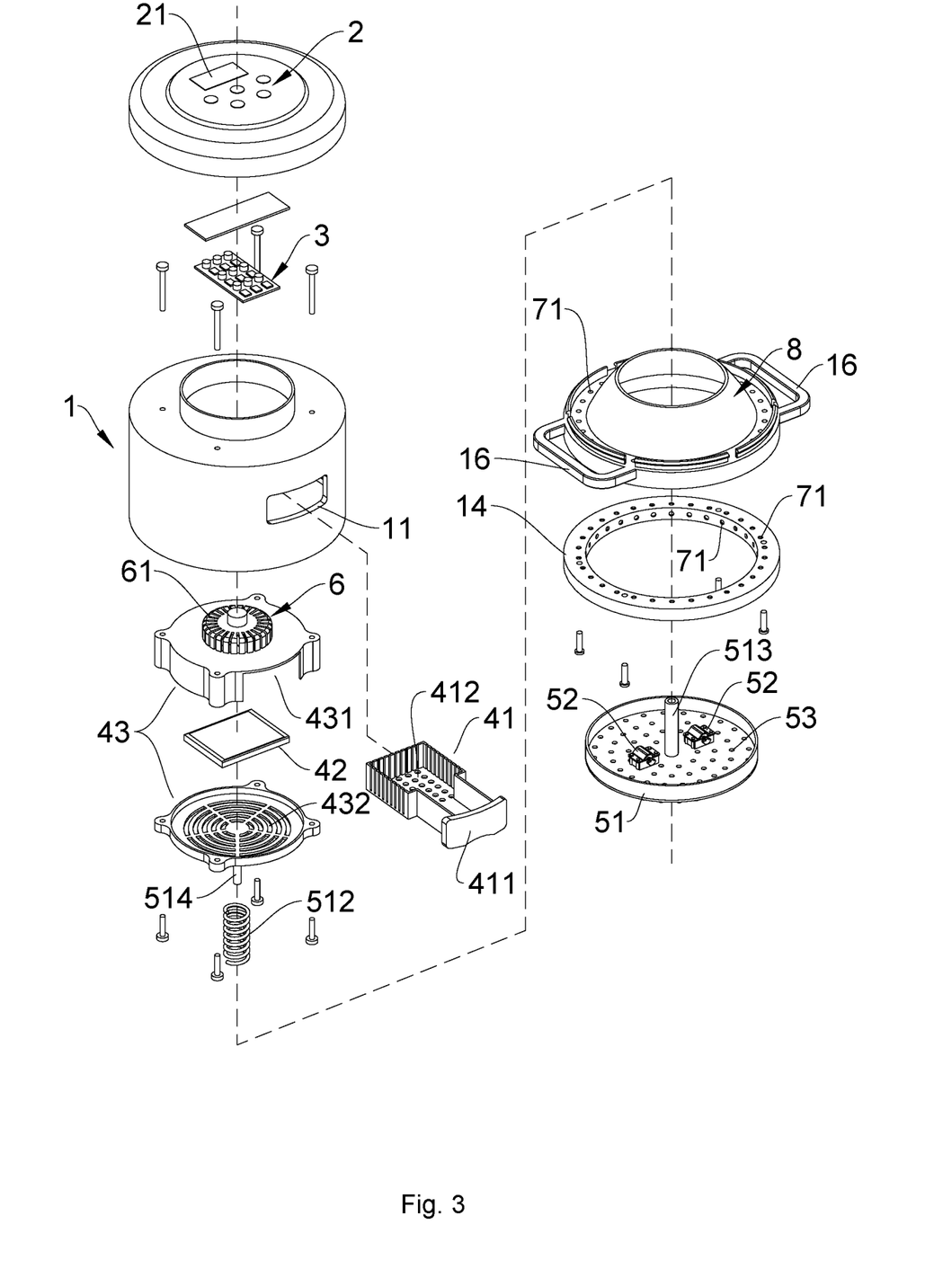
FIG. 3 is an exploded structural view according to embodiment 1 of the present invention.
Figure 4:
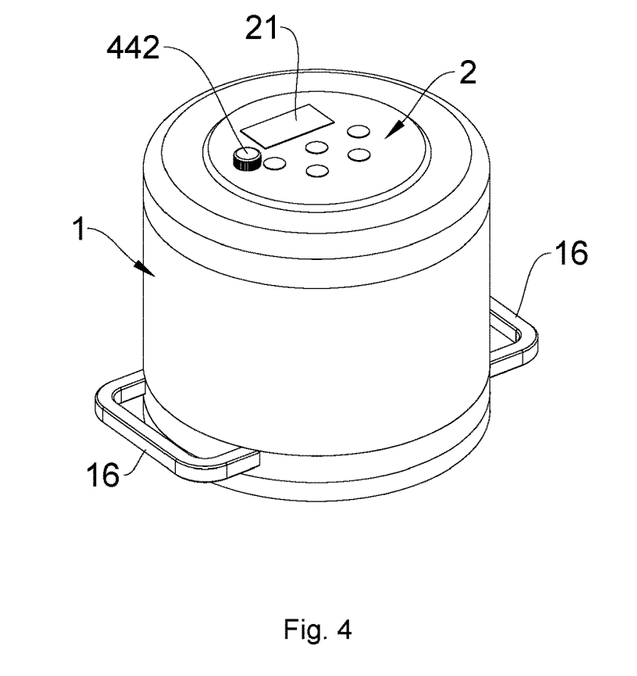
FIG. 4 is a perspective structural view according to embodiment 2 of the present invention.

As shown in FIGS. 2 and 3, the medicine supply mechanism 4 can be implemented as an electrically heating and volatilizing device for solid form medicine, comprising a medicine chamber 41, an electrical heating plate 42, and a supporting shell 43. A detailed preferred embodiment of the medicine supply mechanism 4 is as follows: a mini booster fan 6 is provided on the supporting shell 43; the mini booster fan increases the speed of medicine molecules (or as commonly said in Chinese, the scent of the medicine) blowing towards the targeted body part, so that the targeted body part quickly receives warming from the medicine molecules, thereby resulting in further increased efficiency and effects of the medicinal therapy. An air backflow channel 7 is formed between the supporting shell 43 and the housing 1. One end of the air backflow channel 7 is in communication with an air inlet 61 of the mini booster fan 6; another end of the air backflow channel 7 is in communication with air backflow holes 71 provided around a periphery of a bottom part of the housing. Therefore, the medicine molecules can be circulated between the targeted body part and the ultrasonic medicine application device, as shown by the arrows in FIG. 2 indicating the circulation. As such, loss of the medicine molecules to the outer environment can be effectively reduced, thereby increasing the utility rate of the therapeutically effective medicine molecules, and at the same time reducing the odor of the medicine lingering in the indoor environment. In order to achieve better guiding of the medicine molecules to the targeted body part, the bottom surface of the supporting shell 43 is provided with air openings 432. The electrical heating plate 42 is provided between the air openings 432 and the medicine chamber 41. An air guiding conical element 8 is provided between the supporting shell 43 and the base panel 51 of the ultrasonic massage mechanism 5.

As shown in FIG. 3, in order that the medicine chamber 41 be used for adding in medical tablets, the medicine chamber 41 is configured as a drawer that stores the medical tablets. Specifically, the supporting shell 43 is provided with a groove 431 to accommodate the medicine chamber 41; a side surface of the housing 1 is also provided with an access opening 11; the medicine chamber 41 is inserted into the groove 431 of the supporting shell 43 through the access opening 11. The medicine chamber 41 is formed by a front panel 411 and a medicine storage trough 412.

Figure 5:
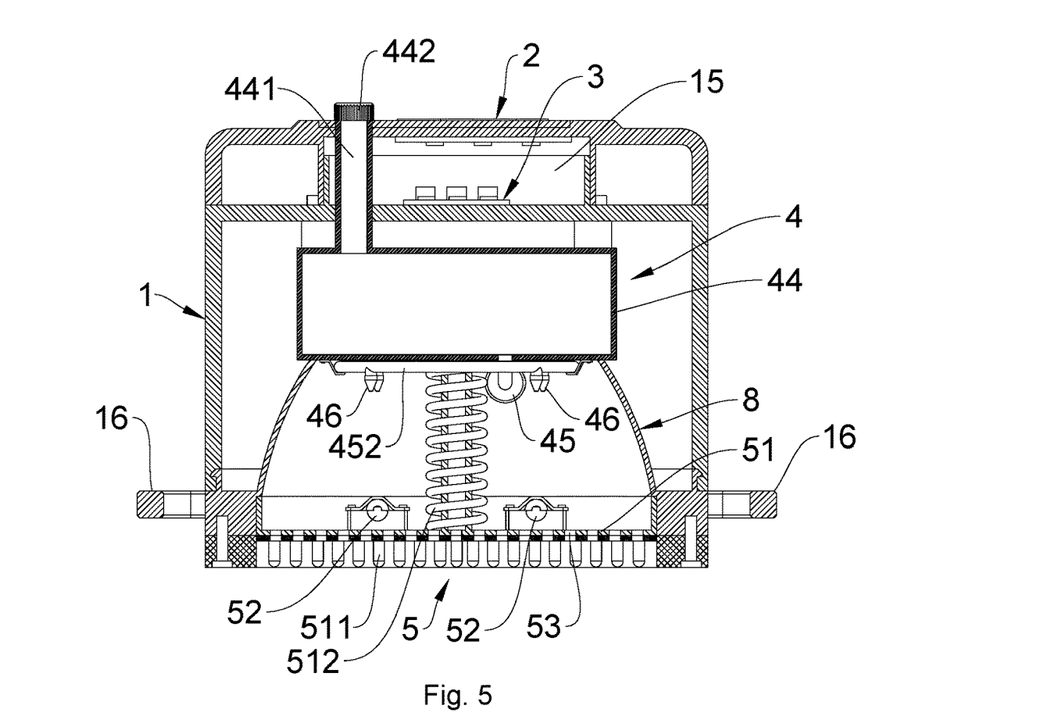
FIG. 5 is a sectional structural view according to embodiment 2 of the present invention.
Figure 6:
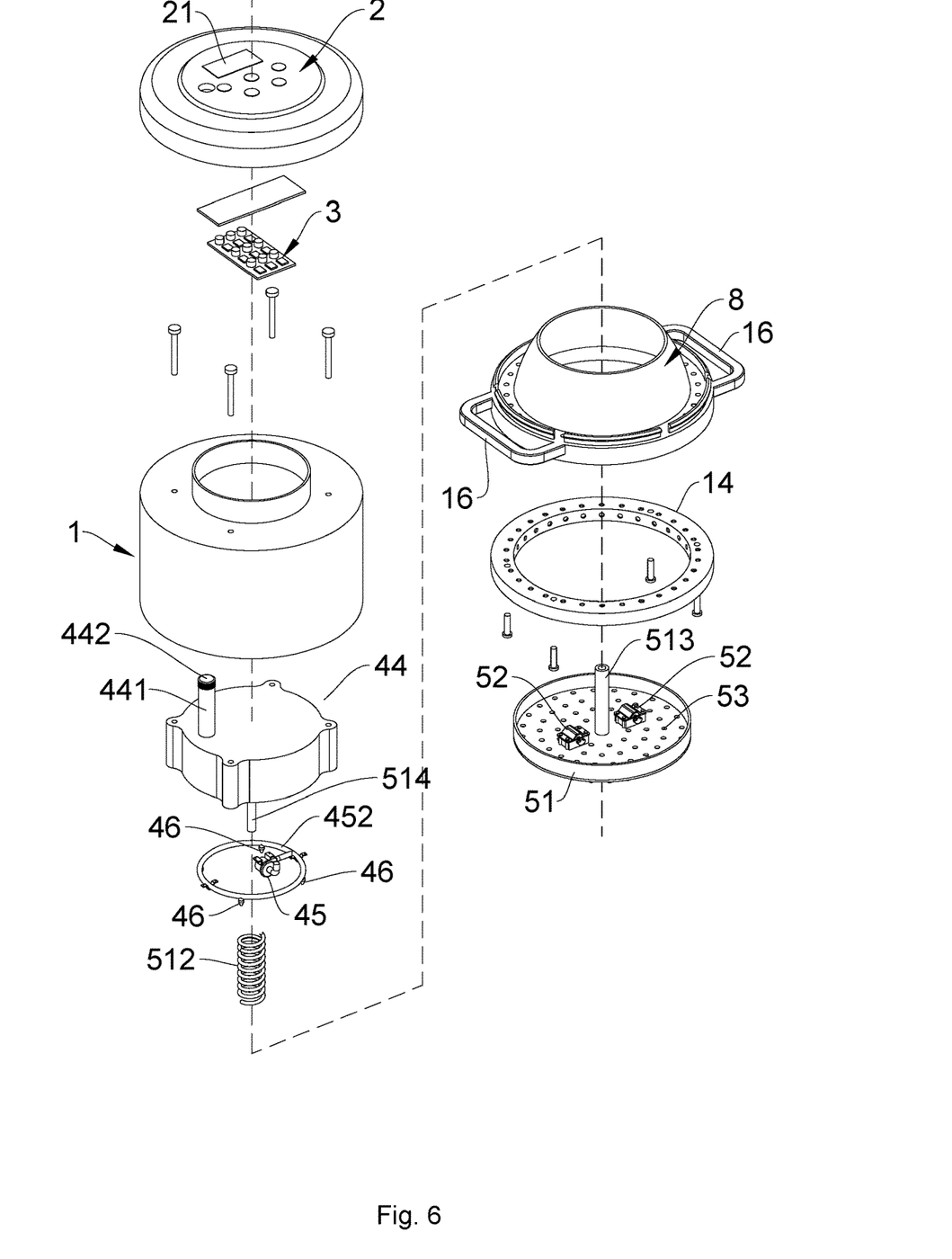
FIG. 6 is an exploded structural view according to embodiment 2 of the present invention.
Figure 7:
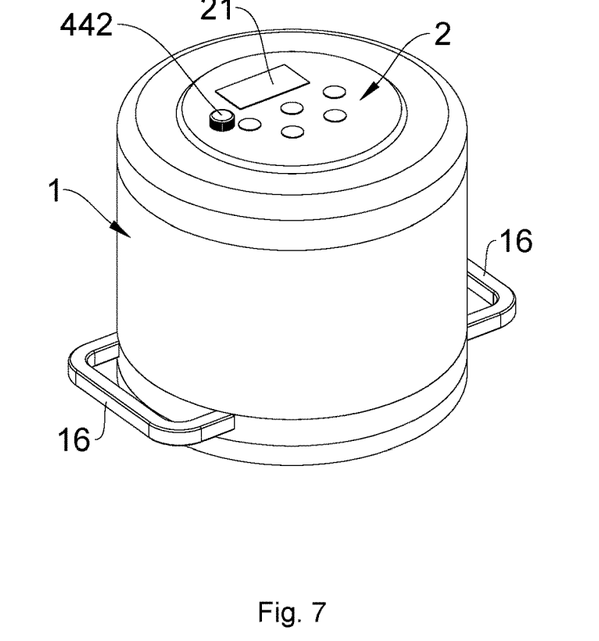
FIG. 7 is a perspective structural view according to embodiment 3 of the present invention.

Alternatively, as shown in FIGS. 5-6, the medicine supply mechanism 4 can be implemented as a liquid form medicine spraying device, comprising a liquid storage box 44, a liquid suction pump 45 and a plurality of mist spray nozzles 46. A detailed preferred embodiment of this kind of medicine supply mechanism 4 is as follows: the liquid storage box 44 is provided with a liquid adding inlet 441; the liquid adding inlet 441 is extended so that one end thereof is exposed out of the housing 1; the end of the liquid adding inlet exposed out of the housing is provided with a cap 442. The liquid suction pump 45 is provided on an outer bottom surface of the liquid storage box 44; a liquid inlet end of the liquid suction pump 45 is connected with the liquid storage box 44; a liquid outlet end of the liquid suction pump 45 is connected with a circular liquid tube 452. The mist spray nozzles 46 that spray the medicine as mist towards the ultrasonic massage mechanism 5 are provided on the circular liquid tube 452.

Figure 8:
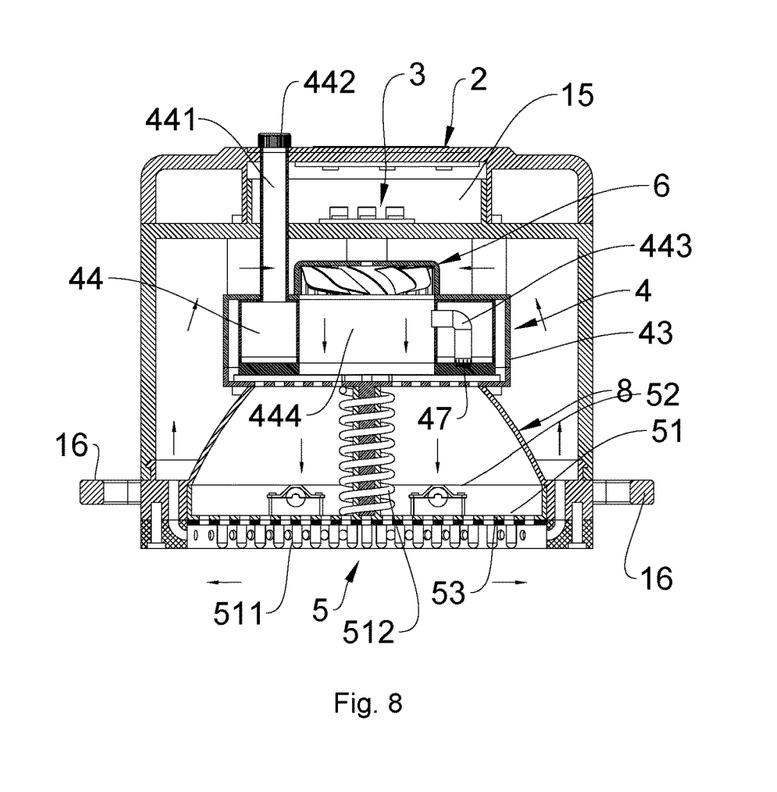
FIG. 8 is a sectional structural view according to embodiment 3 of the present invention.
Figure 9:
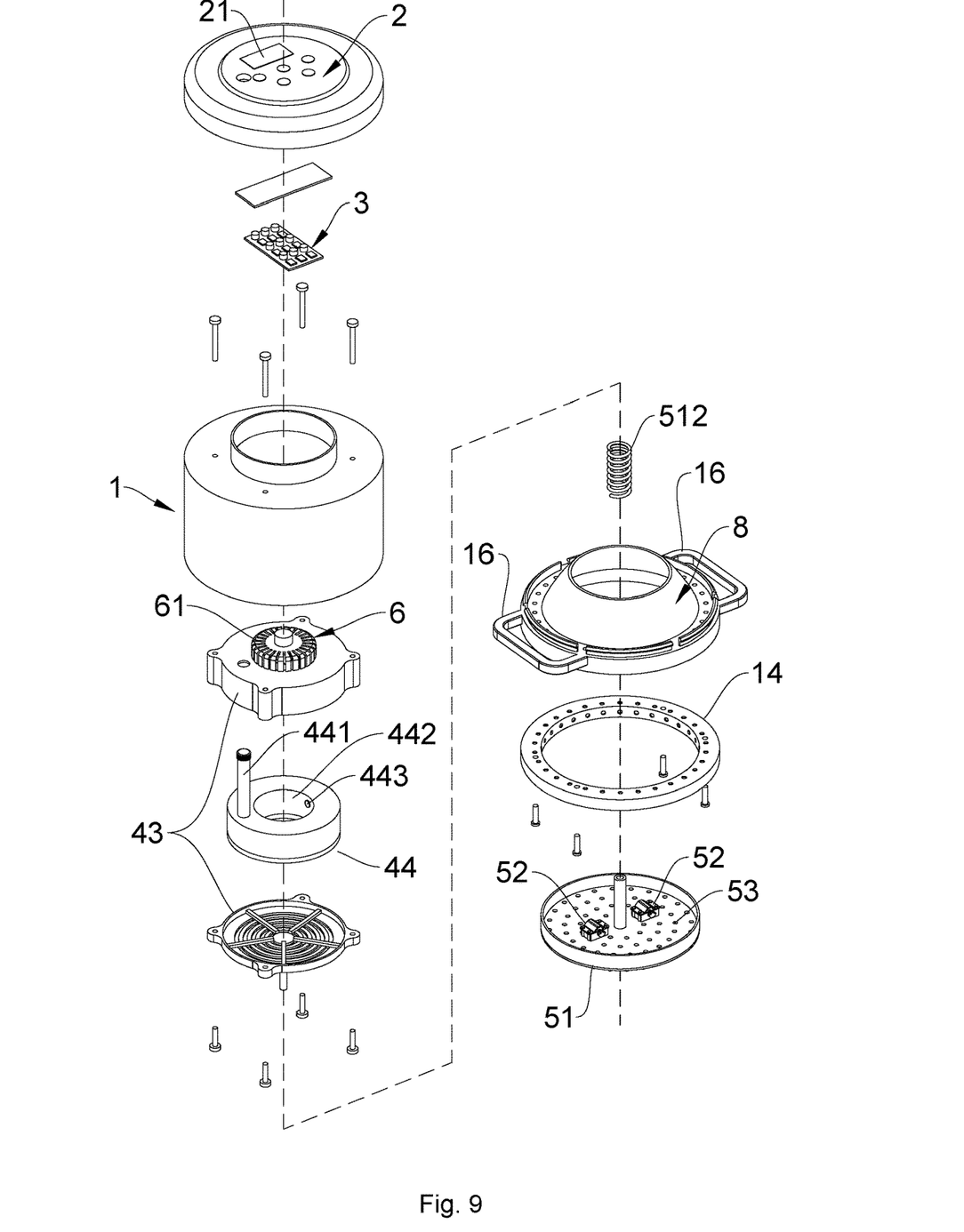
FIG. 9 is an exploded structural view according to embodiment 3 of the present invention.
Figure 10:
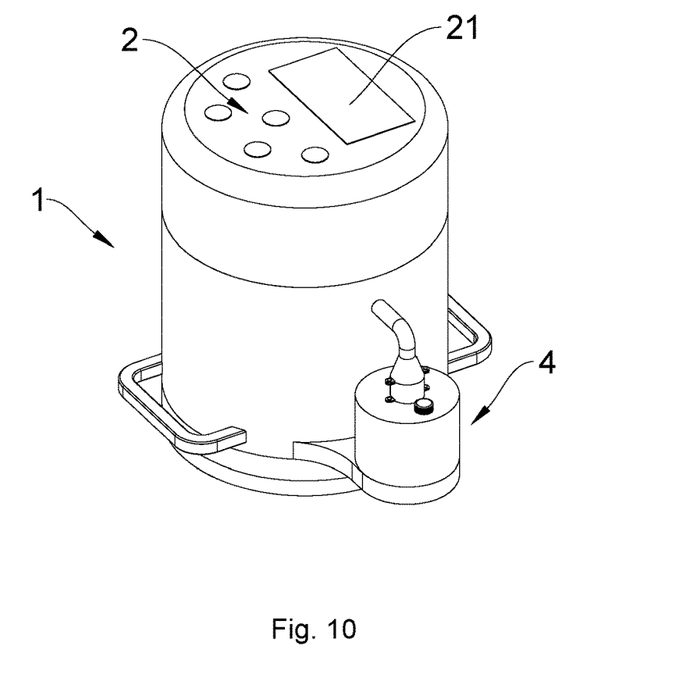
FIG. 10 is a perspective structural view according to embodiment 4 of the present invention.

Alternatively, as shown in FIGS. 8-9, the medicine supply mechanism 4 can be implemented as an ultrasonically atomized liquid form medicine spraying device, comprising a supporting shell 43, a liquid storage box 44, and an ultrasonic atomizing module 47. A detailed preferred embodiment of this kind of medicine supply mechanism 4 is as follows: A liquid adding inlet 441 is provided on the liquid storage box 44; the liquid storage box 44 is provided with a liquid adding inlet 441; the liquid adding inlet 441 is extended so that one end thereof is exposed out of the housing 1 in order to facilitate replenishment of the liquid form medicine; the end of the liquid adding inlet exposed out of the housing is provided with a cap 442 to prevent the liquid form medicine from spilling out during use. The ultrasonic atomizing module 47 is provided on the liquid storage box 44 and is in communication with the inside of the liquid storage box 44; a mist guiding tube 443 is also provided on the liquid storage box 44. Further, a mist guiding channel 444 is provided on the liquid storage box 44; the mist guiding channel 443 is in communication with the mist guiding tube 443; a bottom end of the mist guiding channel 444 is configured towards the ultrasonic massage mechanism 5. A mini booster fan 6 is provided above the mist guiding channel 444; an air guiding conical element 8 is provided between the supporting shell 43 and the base panel 51 of the ultrasonic massage mechanism 5; a top end of the air guiding conical element 8 is in communication with the mist guiding channel 444. FIGS. 8-9 illustrate the liquid storage box 44 being provided internally within the housing.

Figure 11:
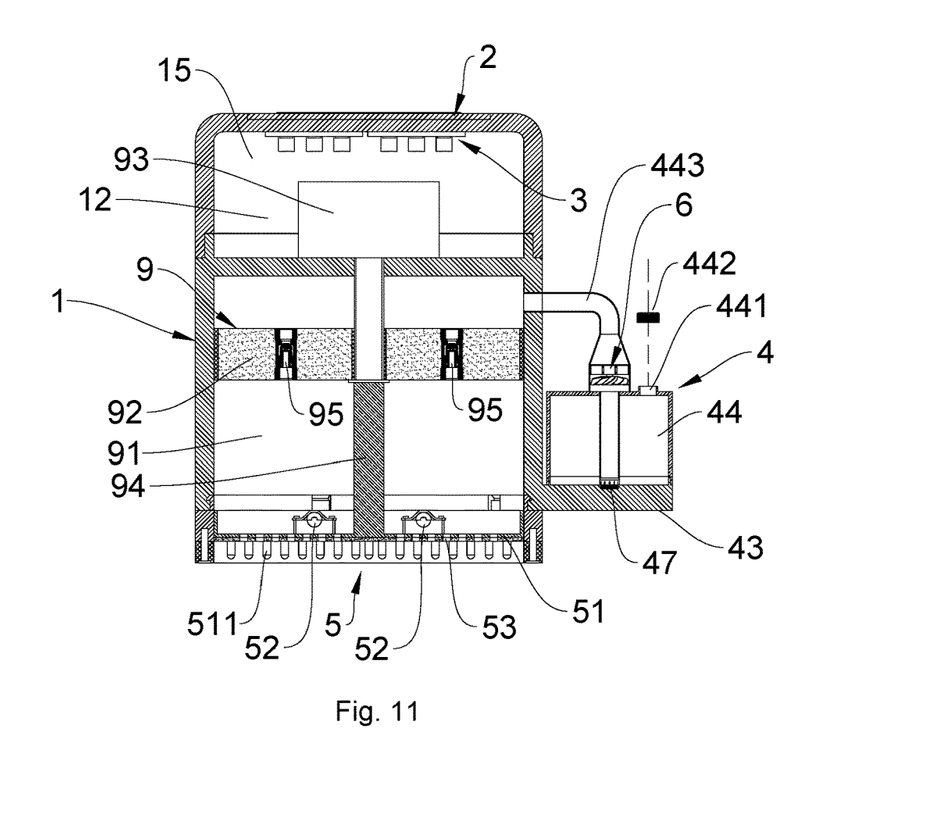
FIG. 11 is a sectional structural view according to embodiment 4 of the present invention.
Figure 12:
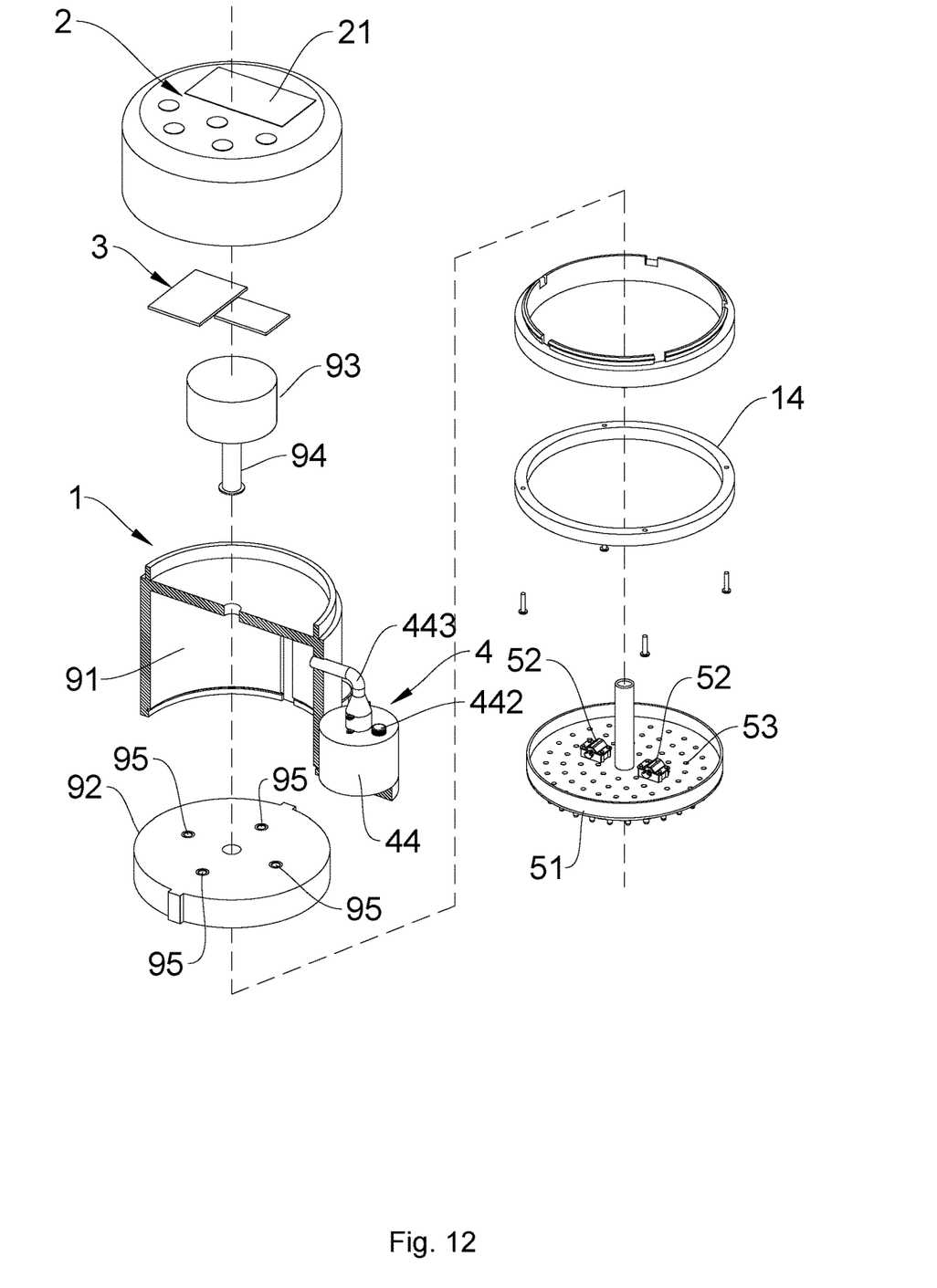
FIG. 12 is an exploded structural view according to embodiment 4 of the present invention.
Figure 13:
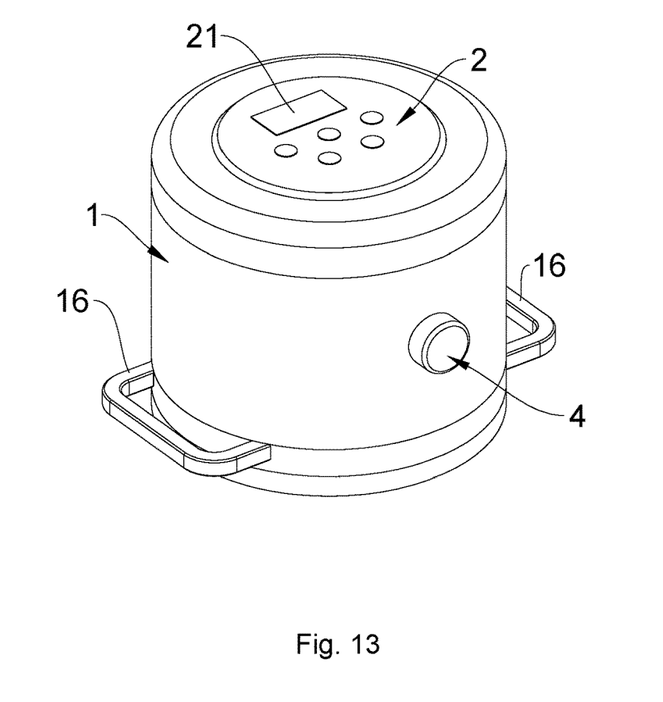
FIG. 13 is a perspective structural view according to embodiment 5 of the present invention.

Further to the above described embodiment, apart from being provided internally within the housing, the liquid storage box 44 may also be provided externally out of the housing, and a detailed preferred embodiment thereof is as follows: As shown in FIGS. 11-12, the liquid storage box 44 is provided on the housing 1; a liquid adding inlet 441 is provided on the liquid storage box 44; one end of the liquid adding inlet is exposed out of the liquid storage box 44; the end of the liquid adding inlet exposed out of the liquid storage box is provided with a cap 442. The ultrasonic atomizing module 47 is provided on the liquid storage box 44 and is in communication with the inside of the liquid storage box 44; the liquid storage box 44 is also provided with a mist guiding tube 443. In order that the atomized medicine can quickly come into contact with the patient's skin, a piston assembly 9 is provided inside the housing 1, as shown in FIGS. 11-12. The piston assembly 9 comprises a piston chamber 91, a piston 92, a piston driving motor 93 and a screw 94, all being provided inside the housing 1. The piston driving motor 93 is a DC powered push rod motor that achieves a short stroke. The piston driving motor 93 is provided inside a cavity 12 provided inside the housing 1. The screw 94 is mounted inside the piston chamber 91 and is connected with the piston driving motor 93. The piston 92 is inserted into the piston chamber 91 and is connected with the screw 94, so that when the piston 92 is driven by the piston driving motor 93, the piston 92 will move up and down inside the piston chamber 91. A one-way valve 95 is provided on the piston 92. The mist guiding tube 443 is in communication with the piston chamber 91. A mini booster fan 6 is provided inside the mist guiding tube 443 to facilitate the flow of atomized medicine to the piston chamber 91. During use, by driving the piston 92 downwardly using the piston driving motor 93, the atomized medicine at a bottom part of the piston chamber 91 will be pushed towards the ultrasonic massage mechanism 5. The atomized medicine then passes through the through holes 53 of the base panel 51 and quickly comes into contact with the patient's skin. When the piston 92 reaches or is proximal to the ultrasonic massage mechanism 5, the piston driving motor 93 will run reversely, and thus the piston 92 will be driven upwardly to reset. While the piston is driven upwardly to reset, the one-way valve 95 is simultaneously open so that the atomized medicine at a first side of the piston facing towards an upper part of the piston chamber will flow to a second side of the piston facing towards the bottom part of the piston chamber through the one-way valve of the piston 92. As such, the atomized medicine now at the bottom part of the piston chamber is ready to be pushed towards the ultrasonic massage mechanism when the piston is once again being driven to move downwardly. Accordingly, by means of reciprocating up and down movements of the piston 92, the atomized medicine is transported from the first side of the piston 92 to the second side of the piston 92. When the piston 92 moves to the upper end of the piston chamber 91, the piston driving motor 93 will once again reverse its running direction to run positively, so that the piston 92 will be once again driven to move downwardly to push the atomized medicine towards the ultrasonic massage mechanism 5. Therefore, the atomized medicine is pushed to contact with the patient's skin every time when the piston is driven downwardly. The one-way valve 95 is operated electrically or mechanically.

Figure 14:
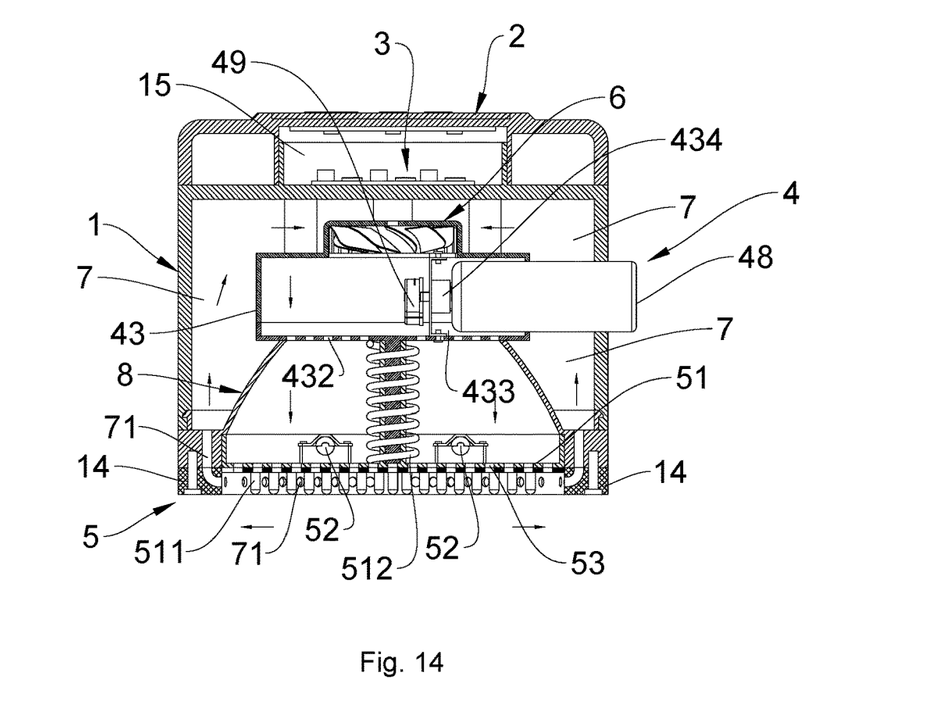
FIG. 14 is a sectional structural view according to embodiment 5 of the present invention.
Figure 15:
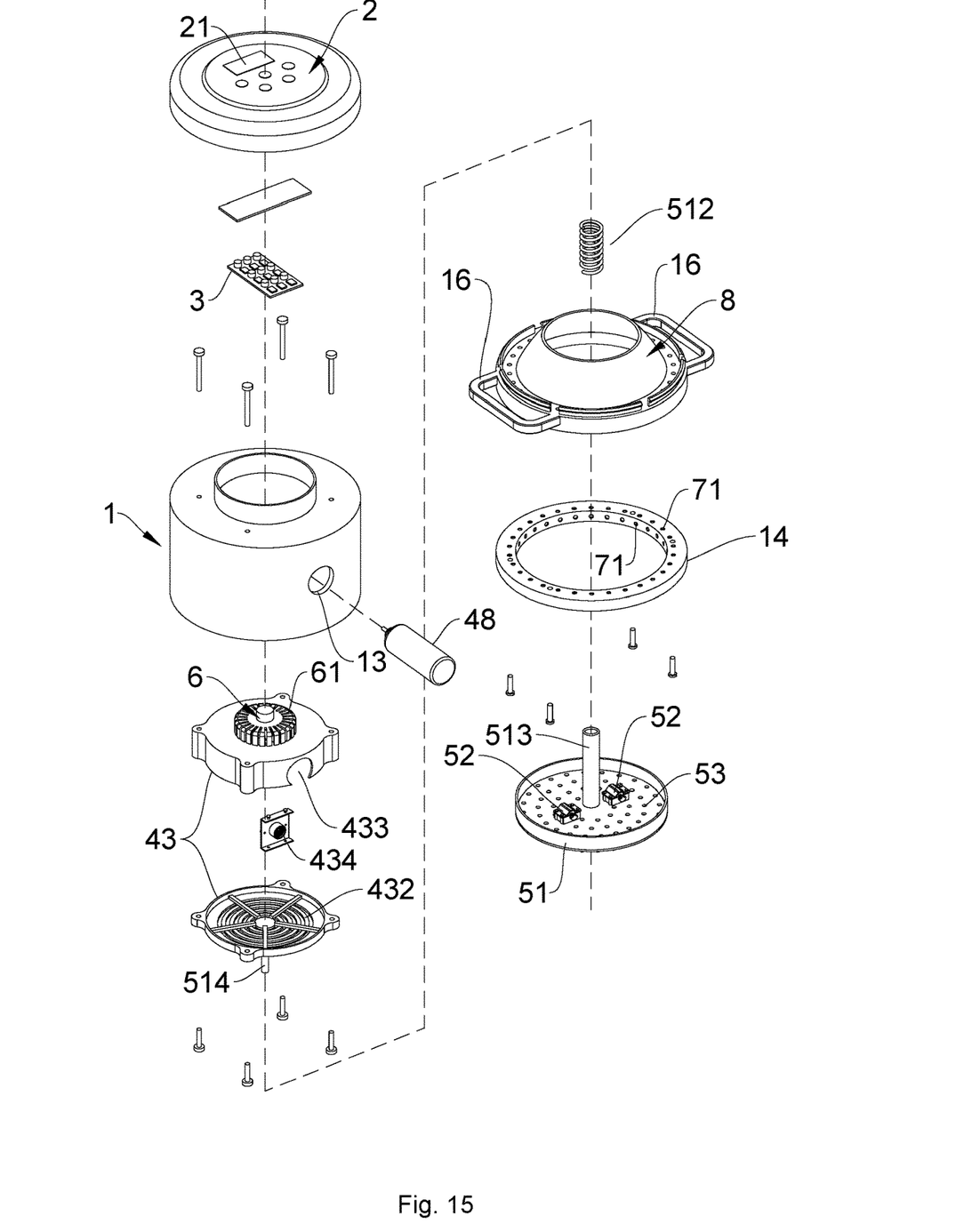
FIG. 15 is an exploded structural view according to embodiment 5 of the present invention.

Alternatively, as shown in FIGS. 14-15, the medicine supply mechanism 4 can be implemented as an electrical heating and volatilizing device for liquid form medicine, comprising a supporting shell 43, a liquid storage container 48, an electrical heating ring 49, and a liquid suction body 50, wherein one end of the liquid suction body 50 is configured to be inserted into the liquid storage container 48, and another end of the liquid suction body 50 is configured to be sleeved within the electrical heating ring 49. A detailed preferred embodiment of this kind of medicine supply mechanism 4 is as follows: As shown in FIGS. 14-15, an insertion groove 433 is provided inside the supporting shell 43; a threaded connecting port 434 is provided inside the insertion groove 433. The electrical heating ring 49 is disposed on the supporting shell 43 at an end of the threaded connecting port 434 opposite to an opening of the insertion groove 433 on the supporting shell 43. A side surface of the housing 1 is provided with an insertion opening 13 at a position corresponding to the insertion groove 433. The liquid storage container 48 is inserted through the insertion opening 13 into the insertion groove 433 to be threadedly connected with the threaded connecting port 434.

Also, as shown in FIGS. 14-15, a mini booster fan 6 is provided on the supporting shell 43 at a position above the electrical heating ring 49 to achieve increased air stream pressure. Air openings 432 are provided on the supporting shell 43 at a position below the electrical heating ring 49. An air guiding conical element 8 is provided between the air openings 432 on the supporting shell 43 and the base panel 51 of the ultrasonic massage mechanism 5 to guide the air flowing direction. Further, an air backflow channel 7 is formed between the supporting shell 43 and the housing 1. One end of the air backflow channel 7 is in communication with an air inlet 61 of the mini booster fan 6; another end of the air backflow channel 7 is in communication with air backflow holes 71 provided around a periphery of a bottom part of the housing 1. Therefore, the medicine molecules can be circulated between the targeted body part and the ultrasonic medicine application device, as shown by the arrows in FIG. 14 indicating the circulation. As such, loss of the medicine molecules to the outer environment can be effectively reduced, thereby increasing the utility rate of the therapeutically effective medicine molecules, and at the same time reducing the odor of the medicine lingering in the indoor environment.

Figure 16:
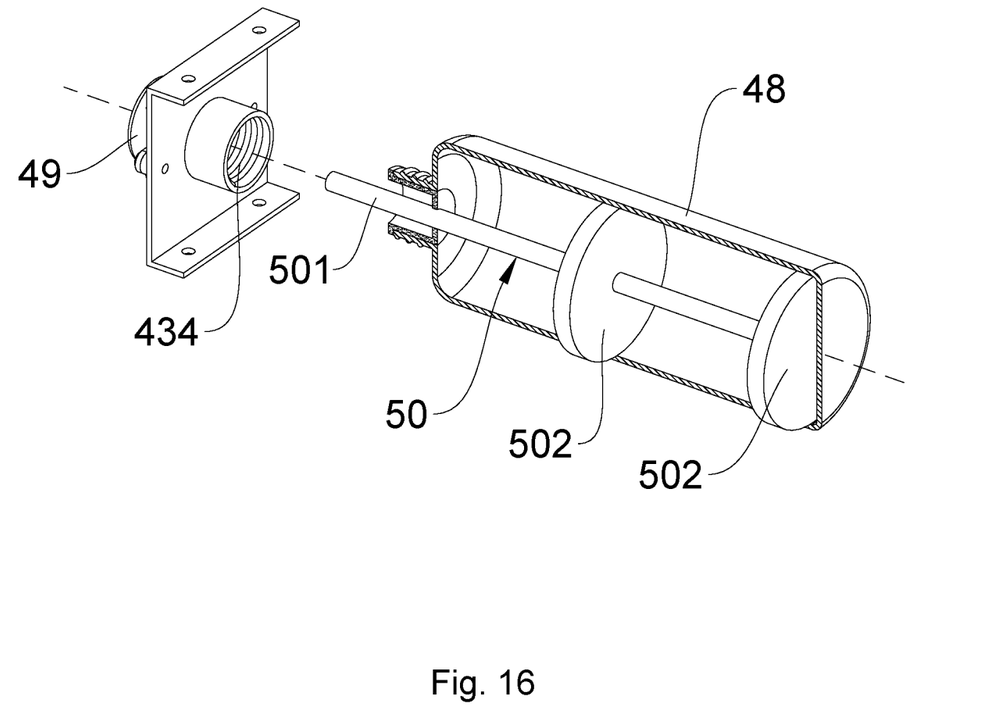
FIG. 16 is a structural view showing installation of the liquid suction rod, the liquid suction and guiding plates, and the liquid storage container according to embodiment 5 of the present invention.

In order that the liquid suction body 50 can suction all the liquid inside the liquid storage container 48 no matter when the liquid storage container 48 is disposed horizontally or vertically, the liquid suction body 50 is formed by a liquid suction rod 501 and liquid suction and guiding plates 502. The liquid suction and guiding plates 502 are provided inside the liquid storage container 48. One end of the liquid suction rod 501 is inserted into the liquid storage container 48 to be connected with the liquid suction and guiding plates 502; another end of the liquid suction rod 501 is sleeved inside the electrical heating ring 49.

As shown in FIGS. 2-3 or FIGS. 5-6, or FIGS. 8-9 or FIGS. 11-12 or FIGS. 14-15, a top surface of the base panel 51 of the ultrasonic massage mechanism 5 is provided with a flexible resilience mechanism comprising a spring 512, a sleeve 513 and a core rod 514, wherein a top end of the core rod 514 is connected to the supporting shell 43; a bottom end of the sleeve 513 is connected to the top surface of the base panel 51; a top end of the sleeve 513 receives insertion of the core rod 514 from a bottom end thereof; the spring 512 winds around the sleeve 513 that sleeves the core rod 514. Due to this flexible resilience mechanism, the base panel 51 and the massage projections 511 thereon can always be in sufficiently close contact with the patient's skin to provide vibration and massage, while not pressing too tightly against the patient's skin. Therefore, vibration and massage are more comfortable, and thereby promoting blood circulation in the body. Besides, a soft rubber gasket ring 14 is provided around the bottom part of the housing 1 to further increase the comfort while using the device of the present invention.

Further, an intelligent IC chip, a Bluetooth communication module, and a WIFI module etc can be put into the circuit board 3 during actual implementation of the present invention. Corresponding control applications can be developed to achieve control by smart phones and tablet computers. Also, during implementation of the embodiments described above, particularly in the embodiment using electrical heating to volatilize the medicine, a temperature sensor should be provided to increase safety during use.

What is claimed is:

1. An ultrasonic medicine application device, comprising a housing (1), a control panel (2), a circuit board (3), a medicine supply mechanism (4), and an ultrasonic massage mechanism (5); wherein, the control panel (2) is provided on a surface of the housing (1); the circuit board (3) is mounted inside the housing (1); the control panel (2) and the circuit board (3) are electrically connected;

the ultrasonic massage mechanism (5) is provided at a bottom surface of the housing (1); the ultrasonic massage mechanism (5) comprises a base panel (51) having massage projections (511), and an electrical ultrasonic vibration element (52) provided on the base panel (51); the electrical ultrasonic vibration element (52) is electrically connected with the circuit board (3); the massage projections (511) make high frequency ultrasonic vibration when being driven by the electrical ultrasonic vibration element (52); the electrical ultrasonic vibration element (52) is a high frequency vibrating motor or an ultrasonic transducer;

the medicine supply mechanism (4) is mounted inside the housing (1) between the circuit board (3) and the ultrasonic massage mechanism (5), and is electrically connected with the circuit board (3); the medicine supply mechanism (4) is configured to supply medicine towards the ultrasonic massage mechanism (5); a plurality of through holes (53) are provided on the base panel (51) to allow the medicine to pass through;

the medicine supply mechanism (4) is implemented as an electrically heating and volatilizing device for solid form medicine, the medicine supply mechanism (4) comprises a medicine chamber (41), an electrical heating plate (42), and a supporting shell (43);

a top surface of the base panel (51) of the ultrasonic massage mechanism (5) is provided with a flexible resilience mechanism comprising a spring (512), a sleeve (513) and a core rod (514), wherein a top end of the core rod (514) is connected to the supporting shell (43); a bottom end of the sleeve (513) is connected to the top surface of the base panel (51); a top end of the sleeve (513) receives insertion of the core rod (514) from a bottom end thereof; the spring (512) winds around the sleeve (513) that sleeves the core rod (514);

a soft rubber gasket ring (14) is provided around the bottom part of the housing (1).

2. The ultrasonic medicine application device of claim 1, wherein in the medicine supply mechanism (4) implemented as the electrically heating and volatilizing device for solid form medicine, a mini booster fan (6) is provided on the supporting shell (43); an air backflow channel (7) is formed between the supporting shell (43) and the housing (1); one end of the air backflow channel (7) is in communication with an air inlet (61) of the mini booster fan (6); another end of the air backflow channel (7) is in communication with air backflow holes (71) provided around a periphery of a bottom part of the housing (1).

3. The ultrasonic medicine application device of claim 2, wherein in the electrically heating and volatilizing device for solid form medicine, the medicine chamber (41) is configured as a drawer that stores the medicine; the supporting shell (43) is provided with a groove (431) to accommodate the medicine chamber (41); a side surface of the housing (1) is also provided with an access opening (11); the medicine chamber (41) is inserted into the groove (431) of the supporting shell (43) through the access opening (11); the medicine chamber (41) is formed by a front panel (411) and a medicine storage trough (412).

4. The ultrasonic medicine application device of claim 3, wherein air openings (432) are provided at a bottom surface of the supporting shell (43); the electrical heating plate (42) is provided between the air openings (432) and the medicine chamber (41); an air guiding conical element (8) is provided between the supporting shell (43) and the base panel (51) of the ultrasonic massage mechanism (5).

* * * * *